United States Patent [19]

Fogarty

[11] Patent Number: 4,621,636
[45] Date of Patent: Nov. 11, 1986

[54] ENDARTERECTOMY METHOD AND APPARATUS

[76] Inventor: Thomas J. Fogarty, 770 Welch Rd., Palo Alto, Calif. 94304

[21] Appl. No.: 214,015

[22] Filed: Dec. 8, 1980

Related U.S. Application Data

[63] Continuation of Ser. No. 60,000, Jul. 23, 1979, abandoned.

[51] Int. Cl.⁴ .............................................. A61B 17/32
[52] U.S. Cl. ..................................... 128/304; 128/305
[58] Field of Search .................. 128/303 R, 304, 305, 128/347, 348, 330, 772, DIG. 9, 753, 754, 757

[56] References Cited

U.S. PATENT DOCUMENTS

| | | | |
|---|---|---|---|
| 2,661,003 | 12/1953 | Devine et al. | 128/303 R |
| 2,788,787 | 4/1957 | Trace | 128/303 R |
| 2,944,552 | 7/1960 | Cannon | 128/304 |
| 3,459,188 | 8/1969 | Roberts | 128/347 |
| 4,033,331 | 7/1977 | Guss et al. | 128/DIG. 9 X |

Primary Examiner—Michael H. Thaler
Attorney, Agent, or Firm—Limbach, Limbach & Sutton

[57] ABSTRACT

An annular knife is pulled through an occluded artery. The knife is attached to a tangential wire which extends through a guidance catheter emplaced along the boundary line of occlusion and undiseased artery.

5 Claims, 7 Drawing Figures

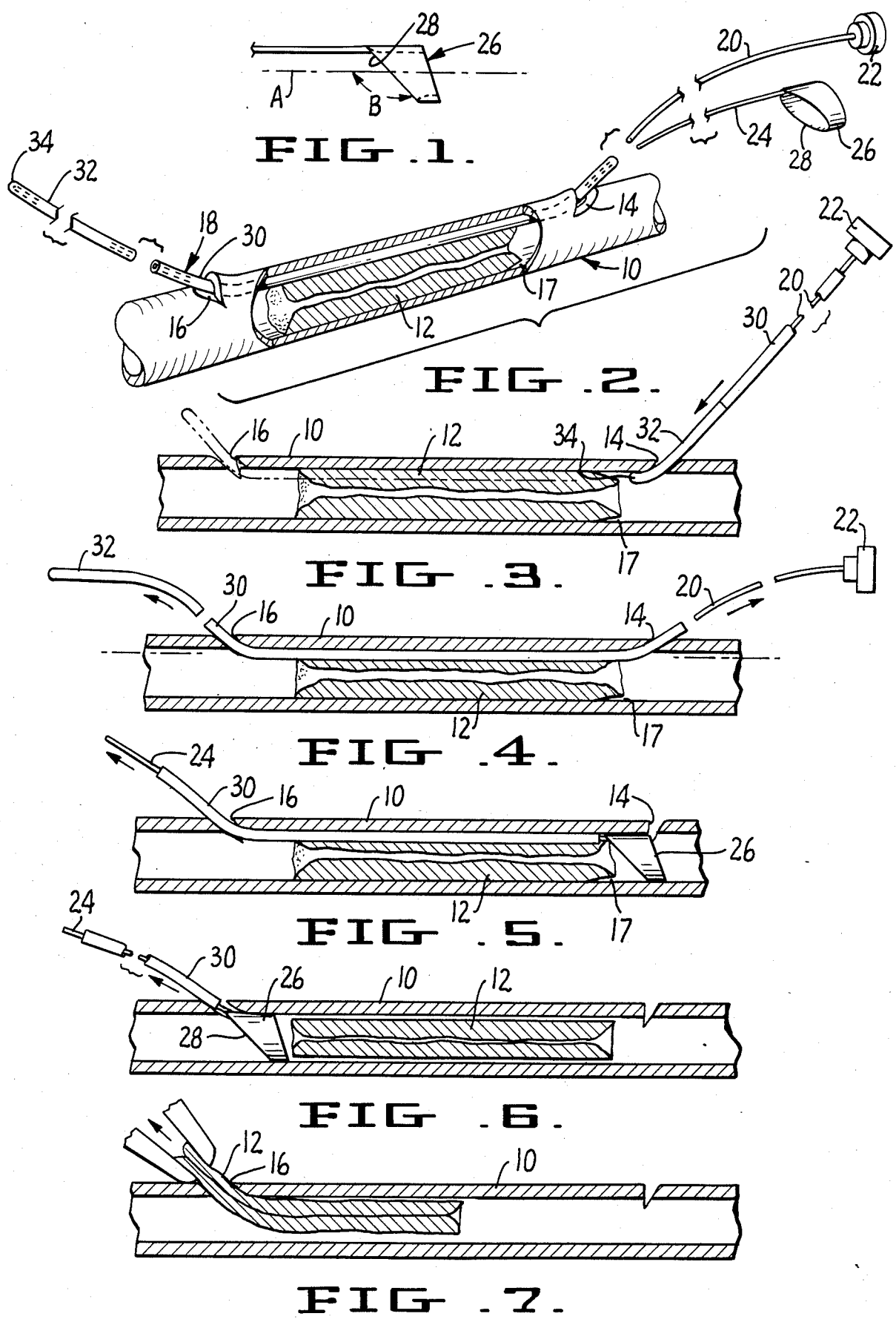

4,621,636

ENDARTERECTOMY METHOD AND APPARATUS

This application is a continuation of application Ser. No. 060,000, filed July 23, 1979, abandoned.

BACKGROUND OF THE INVENTION

The invention relates to a method and means for excising an extended length of arteriosclerotic material from the lumen of an occluded artery.

The prior art known to me which is material as to the subject invention consists of U.S. Pat. Nos. 2,944,552 and 3,811,446. The former discloses an endarterectomy instrument where an annular cutting instrument is pushed along the interior of an occluded artery to excise arteriosclerotic material therefrom. The latter discloses apparatus for removing arteriosclerotic material from an artery comprising an oscillating loop which is used to stretch and loosen the adventitia layers from the media layer of the artery.

SUMMARY OF THE INVENTION

Among the general objects of the invention are the following: to decrease operating time and avoid extensive suturing in the performance of endarterectomies and to allow for complete removal of atherosclerotic material over the operated segment.

A specific object of the invention is to provide means whereby an annular cutting instrument may be pulled rather than pushed through the interior of an occluded artery and be guided with precision while it is being so moved.

A further object of the invention is to provide a method whereby this may be accomplished.

BRIEF DESCRIPTION OF THE DRAWINGS

FIG. 1 is an elevational view of the annular cutting knife of the invention and the drawing wire therefor, with part of the wire broken away;

FIG. 2 is a view in perspective of the apparatus of the invention in associated relation with an occluded artery;

FIG. 3 is a view in diametral section through the occluded artery illustrating the method of placement of the catheter guide means for the cutting instrument;

FIG. 4 is a similar view showing the final stage of emplacement of the catheter guide means;

FIG. 5 is a similar view showing the cutting instrument in associated relation with the catheter guide means and positioned to commence the operation;

FIG. 6 is a similar view showing the catheter guide means and cutting instrument at the end of the operation and prior to their complete removal from the artery; and, FIG. 7 is a similar view illustrating removal of the detached atheroma from the artery.

DESCRIPTION OF THE PREFERRED EMBODIMENT

In the drawing, the artery 10 contains a section of arteriosclerotic material 12 and is provided with a proximal incision 14 adjacent one end of the material 12 and a distal incision 16 adjacent the other end of this material. As shown in the drawing, preparatory to the onset of application of the method and apparatus of the invention, an annular plane 17 is cut around the proximal end of the atheroma 12.

The subject apparatus comprises a catheter 18, a catheter emplacement wire 20 having an annular knob-like handle element 22, concentric with wire 20, and a knife-carrier, or operating, wire 24 terminating in an annular knife 26. The knife 26 is similar to the cutting member 3 shown in U.S. Pat. No. 2,944,552 except that it is reversed in its orientation to the carrier wire so that the cutting edge 28 is directed toward the carrier wire rather than away from the wire. Cutting edge 28 is disposed in a plane which defines with wire 24 an obtuse included angle.

Catheter 18 in its preferred form is split into two sections 30 and 32, the latter having a closed distal end 34.

The catheter is emplaced as follows: The two catheter sections 30 and 32 are sleeved on the emplacement wire 20 so that the proximal end of section 18 abuts the handle element 22 and so that the two catheter sections are in abutting engagement. In this condition, the wire 20 terminates just short of the closed end 34 of the distal section 32 of the catheter to insure that the guide wire will not puncture the closed end 34 as the catheter is emplaced. The emplacement procedure is based upon the concept of using the catheter to establish a straight dividing line between the material 12 and the undiseased layers of the artery 10, a concept which is based upon the facts that the line of least resistance for the catheter is along the interface of 12 and 10 and that the interface approximates a straight line. Emplacement is accomplished by introducing the closed end 34 of the catheter through the proximal incision 13 and then advancing the catheter between the layers of atheroma and artery. The leading end of the catheter is passed through the incision 16. Movement of the catheter is continued until the distal end of proximal section 30 of the catheter has emerged from the incision 16. The distal section 32 of the catheter is then removed from the wire 20. The section portion 30 of the catheter is shown in its final emplaced position in FIG. 1.

As an alternative to the above-described arrangement, the catheter may be of one-piece construction having a closed end 34 and a total length equal to the composite length of the sections 30 and 32. In this case, the catheter is placed by the same technique and cut in two when the placement wire is withdrawn as in FIG. 4. Use at the outset of a two-piece catheter avoids the need of performing a catheter-cutting operation during surgery.

After placement of the catheter section 30, the cutting instrument is associated with the catheter by passing the carrier wire 24 through the section 30 to bring the knife 26 adjacent the proximal end of the catheter. The knife is then worked through the incision 14 to bring it into the position shown in FIG. 5 in which it is adjacent the proximal end of the atheroma 12. The knife 26 is then drawn into the plane 17 to position the knife for the endarterectomy function.

The catheter and cutting instrument 24, 26 are then moved together to effect a cutting away of the material 12 from the artery 10, as shown in FIG. 6. The instrument is then withdrawn through the distal incision 16. Following this, the detached atheroma is removed from the artery as illustrated in FIG. 7.

The catheter may be made from any suitable flexible plastic material. Dacron is a preferred material and polyvinyl chloride is another. A typical O.D. for the catheter is 0.050 inches; a typical I.D. is 0.025 inches.

Typical O.D. dimensions for the wires 20 and 24 are 0.020 and 0.018 inches, respectively.

The wires are made of stainless spring steel. The cutting knife 26 is made from a section of stainless steel tubing and it is silver-soldered to the wire 24, as described in U.S. Pat. No. 2,944,552. As an alternative, the knife may be made of molded plastic joined to the wire by any suitable fastener. Typical dimensions for the knife are 0.250 O.D. with a 0.010 wall thickness. These dimensions will be chosen so as to accomodate the artery diameter.

CONCLUSION

Although a preferred embodiment of the invention has been illustrated and described, it should be understood that the invention is not intended to be limited to the specifics of that embodiment, but rather is defined by the accompanying claims.

What is claimed is:

1. An endarterectomy instrument comprising a catheter and a guide wire, said catheter being split along its length into a distal portion having a closed distal end and a proximal portion, said portions being adapted to be disposed in end to end abutting but disconnected relation, said guide wire freely extending through both portions for substantially the full length thereof, said guide wire having affixed to its proximal end a handle member which is adapted to be engaged with the proximal end of the proximal portion of said catheter, an annular knife, and a wire carrier for said knife having a generally tangential relation therewith, whereby, after emplacement of said catheter along the interface of artery and atheromatous occlusion with said guide wire and removal of the distal portion of said catheter from said guide wire and removal of said guide wire from the proximal portion of said catheter, said wire carrier is adapted to be inserted in the emplaced proximal portion of said catheter up to said knife to thereby interconnect said wire carrier and said proximal portion of said catheter for one-way movement together.

2. For use with an artery occluded with an extensive length of arteriosclerotic material and having catheter emplacement incisions proximally and distally adjacent said material, a catheter emplaced in off-center relation within said artery along the interface of said material and the wall of said artery and extending for the full length of said material and out of said distally adjacent incision, a carrier wire extending through said catheter, and a cutting loop, having a diameter substantially corresponding to the diameter of the normal lumen of said artery, attached to said carrier wire so that said wire is generally tangentially related to said loop, said loop having a cutting edge at the side thereof which is proximal to said carrier wire, said cutting edge being disposed in a plane which defines with said carrier wire an obtuse included angle, said loop being adapted upon the conjoint pulling movement of said catheter and carrier wire through said distally adjacent incision to excise said material from said artery.

3. A method for removing arteriosclerotic occlusions from arteries comprising forming proximal and distal incisions in an artery adjacent an occlusion, introducing a catheter through the proximal incision and feeding it longitudinally of said artery in off-center relation thereto along the interface of said occlusion and said artery to so emplace the same and to extend the distal end of said catheter out of the distal incision while at the same time the proximal end of said catheter extends out of said proximal incision, providing a cutting loop attached generally tangentially to a carrier wire, said loop having a cutting edge at the side thereof which is proximal to said carrier wire, said cutting edge being disposed in a plane which defines with said carrier wire an obtuse included angle, threading said wire into and through said catheter and threading said catheter and wire along said artery so as to position said loop adjacent the proximal end of said occlusion, thereafter moving said catheter and carrier wire by pulling the same along said artery and through said distal incision to excise said occlusion with said loop, and removing the excised occlusion through said distal incision.

4. A method for excising arteriosclerotic occlusions from arteries comprising longitudinally positioning a catheter in off-center relation along the interface of occlusion and artery, placing a cutting loop having a cutting edge within said artery adjacent said occlusion in position to excise said occlusion as said positioned loop is pulled along said artery, said loop having a carrier wire attached thereto generally tangentially thereof, said carrier wire extending through said catheter, said cutting edge being disposed in a plane which defines with said carrier wire an obtuse included angle, and pulling said carrier wire and catheter along said artery to traverse said occlusion with said loop.

5. A method for excising arteriosclerotic occlusions from arteries comprising longitudinally positioning a flexible wire in off-center relation within an artery along the interface of occlusion and artery, said wire having a cutting loop, provided with a cutting edge, attached thereto in a position to excise said occlusion as said wire is pulled along said artery, said cutting edge being disposed in a plane which defines with said carrier wire an obtuse included angle, and pulling said wire along said artery to excisingly traverse said occlusion with said loop.

* * * * *